(12) United States Patent
Moore et al.

(10) Patent No.: US 7,726,172 B2
(45) Date of Patent: Jun. 1, 2010

(54) TESTING DEVICE FOR ACOUSTIC PROBES AND SYSTEMS

(75) Inventors: G. Wayne Moore, Lyons, CO (US);
James M. Gessert, Loveland, CO (US);
Jason T. Sanders, Johnstown, CO (US);
James Ginther, Boulder, CO (US);
Edward Henry, Thornton, CO (US)

(73) Assignee: Unisyn Medical Technologies, Inc., Golden, CO (US)

( * ) Notice: Subject to any disclaimer, the term of this patent is extended or adjusted under 35 U.S.C. 154(b) by 479 days.

(21) Appl. No.: 11/668,147

(22) Filed: Jan. 29, 2007

(65) Prior Publication Data
US 2007/0234807 A1    Oct. 11, 2007

Related U.S. Application Data

(60) Provisional application No. 60/765,273, filed on Feb. 2, 2006.

(51) Int. Cl.
*G01M 1/14* (2006.01)

(52) U.S. Cl. ............................................. 73/1.82

(58) Field of Classification Search ............... 73/1.82; 714/43
See application file for complete search history.

(56) References Cited

U.S. PATENT DOCUMENTS

| | | | |
|---|---|---|---|
| 2002/0035326 A1* | 3/2002 | Kamiyama | 600/437 |
| 2004/0213417 A1* | 10/2004 | Gessert et al. | 381/66 |
| 2005/0228281 A1* | 10/2005 | Nefos | 600/446 |

* cited by examiner

*Primary Examiner*—Hezron Williams
*Assistant Examiner*—Tamiko D Bellamy
(74) *Attorney, Agent, or Firm*—Townsend and Townsend and Crew LLP

(57) ABSTRACT

A hand-held testing device tests operation of acoustic elements of an acoustic device. The hand-held testing device has a housing, a power supply local to the housing, an acoustic transducer, and circuitry. The circuitry is disposed within the housing and is provided in electrical communication with the power supply and with the acoustic transducer. The circuitry is configured to identify production of a voltage pulse by the acoustic transducer in response to receipt of a received acoustic signal by the acoustic transducer from one of the acoustic elements and to operate the transducer to transmit a transmitted acoustic signal to the acoustic element.

15 Claims, 15 Drawing Sheets

TESTING DEVICE FOR ACOUSTIC PROBES AND SYSTEMS

CROSS-REFERENCES TO RELATED APPLICATIONS

This application is a nonprovisional of U.S. Prov. Pat. Appl. No. 60/765,273, entitled "TESTING DEVICE FOR ACOUSTIC PROBES AND SYSTEMS," filed Feb. 2, 2006 by G. Wayne Moore et al., the entire disclosure of which is incorporated herein by reference for all purposes.

This application is also related to concurrently filed, commonly assigned U.S. patent application Ser. No. 29/276,543, now U.S. Pat. No. D565,444, entitled "TESTING DEVICE FOR ACOUSTIC PROBES AND SYSTEMS," by G. Wayne Moore et al., the entire disclosure of which is also incorporated herein by reference for all purposes.

BACKGROUND OF THE INVENTION

This application relates generally to acoustic probes and systems. More specifically, this application relates to methods and apparatus for testing acoustic probes and systems.

Acoustic imaging techniques have been found to be extremely valuable in a variety of applications. While medical applications in the form of ultrasound imaging are perhaps the most well known, acoustic techniques are more generally used at a variety of different acoustic frequencies for imaging a variety of different phenomena. For example, acoustic imaging techniques may be used for the identification of structural defects, for detection of impurities, as well as for the detection of tissue abnormalities in living bodies. All such techniques rely generally on the fact that different structures, whether they be cancerous lesions in a body or defects in an airplane wing, have different acoustic impedances. When acoustic radiation is incident on an acoustic interface, such as where the acoustic impedance changes discontinuously, it may be scattered in ways that permit characterization of the interface. Radiation reflected by the interface is most commonly detected in such applications, but transmitted radiation is also used for such analysis in some applications.

Transmission of the acoustic radiation towards a target and receipt of the scattered radiation may be performed and/or coordinated with a modern acoustic imaging system. Many modern such systems are based on multiple-element array transducers that may have linear, curved-linear, phased-array, or similar characteristics. These transducers may, for example, form part of an acoustic probe. In some instances, the imaging systems are equipped with internal self-diagnostic capabilities that allow limited verification of system operation, but do not generally provide effective diagnosis of the transmission and receiving elements themselves. Degradation in performance of these elements is often subtle and occurs as a result of extended transducer use and/or through user abuse.

In particular, because modern acoustic systems form images by adding up the contributions of many transducer elements from transducer arrays, the failure of a small number of elements, or a few defective receive channels in the acoustic system, may not be readily perceptible to users. This is a consequence of the averaging effect of summing many elements to form an acoustic beam. But the failure of a small number of elements or receive channels can, nonetheless, significantly degrade the performance of an imaging system, especially in a Doppler mode.

There is accordingly a general need in the art for a convenient, inexpensive, and easy-to-use method for evaluating acoustic probes and systems for failed elements or transmit and receive channels.

BRIEF SUMMARY OF THE INVENTION

Embodiments of the invention thus provide methods and apparatus for testing acoustic probes and systems. In a first set of embodiments, a hand-held testing device is provided for testing operation of acoustic elements comprised by an acoustic device. The hand-held testing device comprises a housing, a power supply local to the housing, an acoustic transducer, and circuitry. The circuitry is disposed within the housing and is provided in electrical communication with the power supply and with the acoustic transducer. The circuitry is configured to identify production of a voltage pulse by the acoustic transducer in response to receipt of a received acoustic signal by the acoustic transducer from one of the acoustic elements and to operate the transducer to transmit a transmitted acoustic signal to the one of the acoustic elements.

In some such embodiments, the acoustic transducer consists of a single acoustic transducer. The transmitted acoustic signal may comprise a plurality of transmitted acoustic signals having different frequencies in some instances. In one such case, the circuitry is further configured to operate the transducer to transmit the plurality of transmitted acoustic signals successively in time. In one embodiment, the circuitry is disposed on a mother board and a daughter board connected with the mother board with a notch assembly.

The acoustic transducer may be shaped and sized to contact the acoustic elements individually. In some embodiments, the acoustic transducer has a generally peak-shaped tip for contacting the acoustic elements. The tip may have an elevational length less than about 1 cm, and in one embodiment has an elevational length between 0.1 and 0.5 cm. In one embodiment, the tip comprises polyvinylidene fluoride.

The hand-held testing device may further comprise a signaling element provided in electrical communication with the circuitry, which is further configured to identify production of the voltage pulse by placing the signaling element into a predetermined state. In some embodiments, the signaling element comprises a plurality of predetermined states, with the circuitry being further configured to identify a failure to produce the voltage pulse by placing the signaling element into a second of the predetermined states. A suitable signaling element may comprise a light-emitting diode.

The housing of the hand-held testing device may be generally cylindrical. It may have a diameter between about 0.2 cm and 5.0 cm, and may have a length between about 4 cm and 30 cm.

In one embodiment, the circuitry is configured to operate the transducer to transmit the transmitted acoustic signal to the one of the acoustic elements substantially synchronously with receipt of the received acoustic signal by the acoustic transducer.

In a second set of embodiments, a method is provided for testing operation of acoustic elements comprised by an acoustic device. A received acoustic signal is received with an acoustic transducer comprised by a hand-held device from one of the acoustic elements. A voltage pulse is generated with the acoustic transducer in response to receipt of the received acoustic signal. Generation of the voltage pulse is identified. A transmitted acoustic signal is transmitted to the one of the acoustic elements with the acoustic transducer.

In some such embodiments, the acoustic transducer consists of a single acoustic transducer. The transmitted acoustic signal may comprise a plurality of transmitted acoustic signals having different frequencies. In certain cases, the plurality of transmitted acoustic signals are transmitted successively in time. Identification of the generated voltage pulse may comprise placing a signaling element comprised by the hand-held device into a predetermined state.

In a third set of embodiments, a method is also provided for testing operation of acoustic elements comprised by an acoustic device. A hand-held device that comprises a transducer is positioned such that the transducer is in contact with one of the acoustic elements. A determination is made whether the acoustic element is operational by observing a state of a signaling element comprised by the hand-held device. The state of the signaling element indicates a result of attempting to receive a first acoustic signal from the one of the acoustic elements with the transducer and to transmit a second acoustic signal with the transducer to the one of the acoustic elements. The hand-held device is moved successively to different ones of the acoustic elements to repeat the step of determining with respect to such different ones of the acoustic elements.

The hand-held device may be generally cylindrical, having a diameter between about 0.2 cm and 5.0 cm and a length between about 4 cm and 30 cm. The signaling element may comprise a light-emitting diode.

In a fourth set of embodiments, a method is provided of testing an operational modality of an acoustic system. The acoustic system is provided in a state configured to generate an image on a display in accordance with the operational modality. The image is derived from input from an acoustic probe in accordance with the state. The acoustic probe is provided in electrical communication with an input to the acoustic system. The acoustic probe has a plurality of acoustic transducers. Each acoustic transducer is adapted to convert an acoustic signal into an electronic signal that is provided to the input. A voltage pulse is generated with a hand-held testing device. The voltage pulse is converted into a test acoustic signal with the testing device. The test acoustic signal is transmitted to the acoustic probe. A diagnostic image is displayed on the display corresponding to a processing of the test acoustic signal by the acoustic probe and the acoustic system in accordance with the state of the acoustic system.

In some of these embodiments, the operational modality comprises a B-mode modality. The absence of a signal in the diagnostic image then indicates the presence of a fault. A position of transmitting the test acoustic signal to the acoustic probe may be translated across the plurality of transducers. In some embodiments, a verification acoustic signal is received from the acoustic probe with the test device. A signaling element of the test device is activated to confirm receipt of the verification signal. The absence of the signal in the diagnostic image then indicates the fault is present in the acoustic system. In some cases, the test signal might comprise a plurality of different frequencies. The diagnostic image may then comprise features generated from multiple of the different frequencies. If the acoustic probe is a narrowband probe, the diagnostic image may consist of features generated from only one of the plurality of different frequencies.

In other embodiments, the operational modality comprises a pulsed-wave Doppler modality. The absence of a Doppler signal in the diagnostic image then indicates the presence of a fault. In some such cases, the state has a pulse repetition frequency between 5.3 and 6.5 Hz. The state may also have a Doppler wall filter of about 200 Hz.

In still other embodiments, the operational modality comprises a color-flow modality with the absence of a color-flow signal in the diagnostic image indicating the presence of a fault. Similarly, the operational modality may comprise a spatial-compounding modality, with the diagnostic image showing a plurality of intersecting beams.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components.

DETAILED DESCRIPTION OF THE INVENTION

1. Testing Device Structure

Embodiments of the invention provide methods and devices that may be used in testing acoustic probes and/or systems. Such acoustic probes and systems are sometimes referred to herein collectively as "acoustic devices." While much of the description below makes use of specific examples in discussing various aspects of the invention, such examples are intended merely for illustrative purposes; the invention is not intended to be limited by any operational characteristics used by the tested probe or system, such as the operational frequency characteristics of the tested acoustic device. As illustrated in further detail below, each of the acoustic probes and systems that may be tested with embodiments of the invention includes a plurality of "transducer elements," which refers to elements adapted to transmit acoustic radiation and/or to receive acoustic radiation. While such elements are referred to generically herein as "transducer elements," reference is sometimes also made herein to "receiver elements" and to "transmitter elements" to distinguish them on the basis of their functions.

Embodiments of the invention provide a self-contained device that may be used in testing the operation of acoustic devices. In many embodiments, the device is advantageously includes a local power source, such as in the form of conventional alkaline batteries, and is of a compact size that permits it to be carried easily by technicians as a hand-held device. The testing device is based on a transducer design that has a small contact area to permit it to interact with, and thereby evaluate the operation of, array transducers one element at a time. The testing-device transducer may advantageously be used both as a transmitter and receiver. To test transmission by an element of the acoustic-device array, it may receive an acoustic pulse generated by that element. To test reception by an element of the acoustic-device array, it may also transmit an acoustic pulse back into the acoustic-device, permitting a verification that an external acoustic signal may be displayed by the acoustic device. The testing device may also include a visual, auditory, or other signaling mechanism to indicate to an operator whether acoustic pulses have been received, and thereby confirm proper operation by the acoustic device. The acoustic device itself may sometimes include a display device on which transmit pulses are displayed within an image field at a depth consistent with the frequency response of the particular transducer then under test.

Figure 1A:
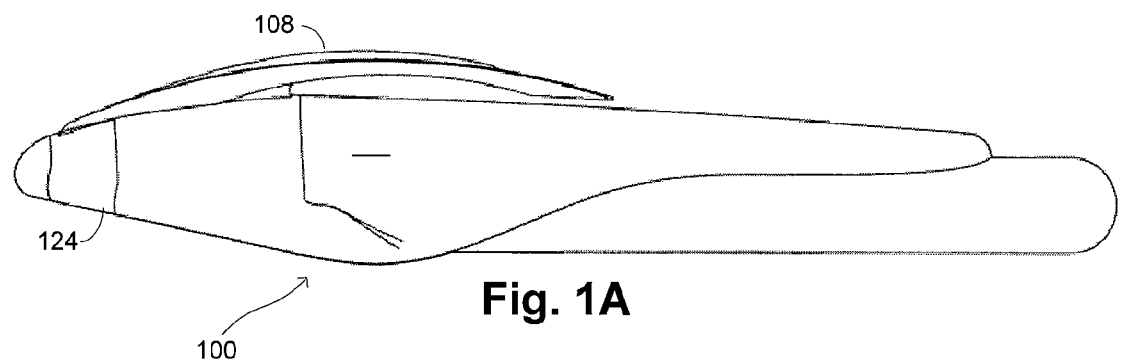
FIG. 1A is a side view of a device for testing acoustic probes and/or systems in accordance with an embodiment of the invention.
Figure 1B:
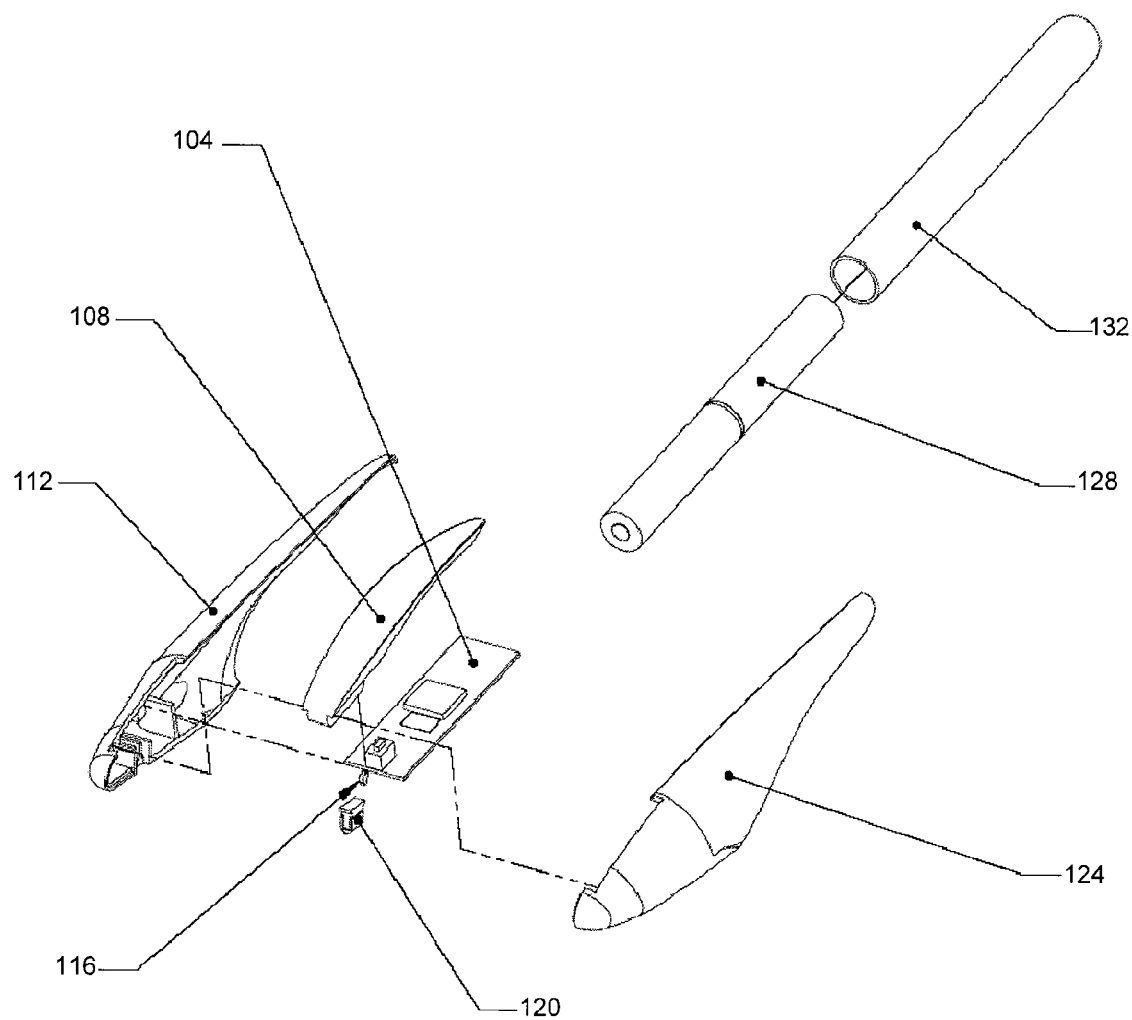
FIG. 1B is an exploded view of the device of FIG. 1A.

A structural overview of a testing device in one embodiment of the invention is provided with FIGS. 1A and 1B. In this embodiment, the testing device is generally cylindrical and has a size similar to that of a medium-sized high-quality ballpoint pen. Merely by way of example, the testing device may have a diameter between about 0.2 cm and 5.0 cm, between about 0.5 cm and 4.0 cm, or between about 1.0 cm and 3.0 cm, and it may have a length between about 4 cm and 30 cm, between about 8 cm and 20 cm, or between about 10 cm and 15 cm in various embodiments. FIG. 1A shows a side view of the testing device 100 while FIG. 1B provides an exploded view to illustrate component parts of the testing device 100 in this embodiment. The size and shape of the testing device 100 in this embodiment makes the device conveniently easy to carry by a technician, and may be produced for relatively low cost. As evident from FIG. 1B, the testing device 100 comprises a housing, which may be provided in a plurality of parts 112 and 124 through a snap-fit or other type of engagement. The parts 112 and 124 of the housing may conveniently be fabricated as molded plastic units. A clip 108 may also be fabricated as a molded plastic unit for snap-fit or other type of engagement with the housing when the testing device 100 is assembled. The clip may provide a mechanism for carrying the testing device 100 in a pocket or elsewhere in a fashion conventionally used for pens.

A battery housing 132 may also be provided, and may be secured by and extend distally from the housing 112 and 124 when the housing is assembled. Such a configuration maintains a generally cylindrical shape for the testing device 100 and provides a receptacle for storage of a local power supply in the form of batteries 128. The battery housing 132 may be fabricated from metal or plastic and may be molded in particular embodiments. Merely by way of illustration, the local power supply may comprise a pair of conventional AAA-sized alkaline batteries in one embodiment.

The local power supply provides power to electronics configured to perform the testing functions described in greater detail below. The electronics may be resident on a circuit board 104 disposed within a cavity formed by the housing 112 and 124 and electrically interfaced with the signaling mechanism 116 and a transducer 120 that is brought into contact with elements of the acoustic device being tested. In the illustrated embodiment, the signaling mechanism 116 comprises a red/green LED that may illuminate in either color depending on a detected state of particular elements of the acoustic device being tested or to signal other information to the operator.

Figure 2A:
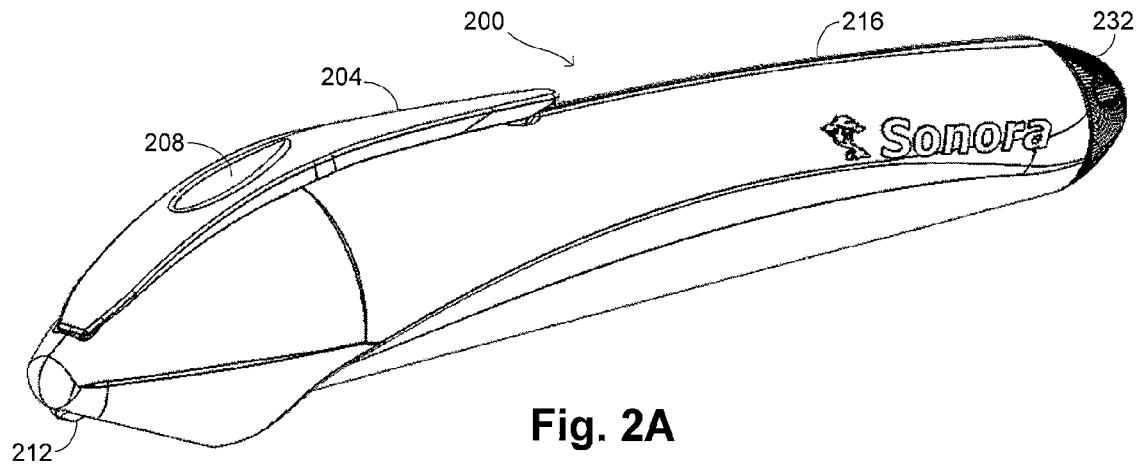
FIG. 2A is a perspective view of a device for testing acoustic probes and/or systems in another embodiment of the invention.
Figure 2B:
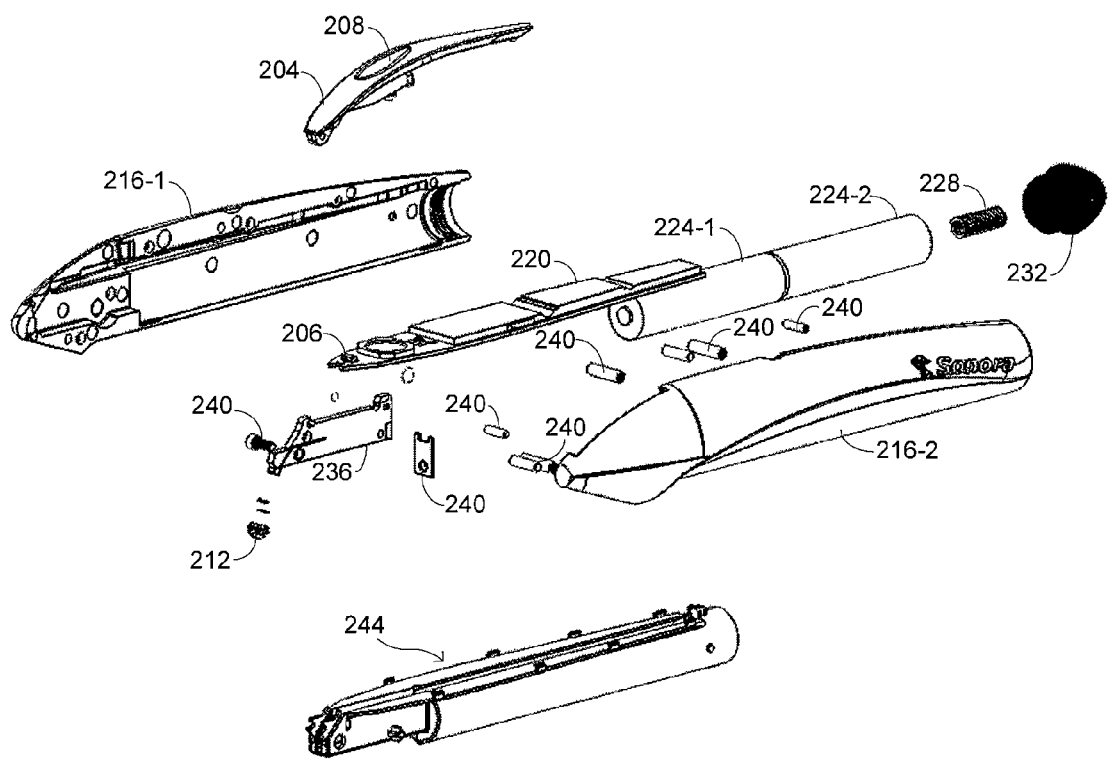
FIG. 2B is an exploded view of the device of FIG. 2A.

An alternative structure for the testing device in an alternative embodiment is illustrated with FIGS. 2A and 2B. A number of aspects of the structure of the testing device 200 in this embodiment are similar to aspects of the structure of the device shown in FIGS. 1A and 1B. For example, the dimensions of the device 200 may be comparable, having a diameter between about 0.2 cm and 5.0 cm, between about 0.5 cm and 4.0 cm, or between about 1.0 cm and 3.0 cm, and having a length between about 4 cm and 30 cm, between about 8 cm and 20 cm, or between about 10 cm and 15 cm in various embodiments. FIG. 2A shows a perspective view of the testing device 200 while FIG. 2B provides an exploded view that illustrates various component parts of the testing device 200 in this embodiment.

As evident from FIG. 2B, the testing device 200 comprises a housing 216 that may be provided in two parts 216-1 and 216-2 that are connected with various pieces of hardware 240 when the device 200 is in the assembled state shown in FIG. 2A. A clip 204 may be fabricated for engagement with the housing 216 and in this embodiment includes a window 208 through which the light-emitting device 206 that acts as a signaling mechanism may be viewed, thereby providing a user with information about a state of an acoustic probe or system. A power supply is also provided in this embodiment in the form of batteries 224 that are secured within the device 200 by a spring 228 and end cap 232. The end cap 232 may be threaded to allow access to replace the batteries 224 when necessary.

In this embodiment, the electronics is advantageously distributed over a pair of circuit boards, a mother board 220 and a daughter board 236 that includes a notch assembly for attachment to the motherboard. Such an arrangement permits the internal electronics to be provided without wires and avoids turmoil that may result from an air-packing arrangement. The light-emitting device 206 may be mounted directly on the mother board 220 and a transducer 212 may be disposed on the edge of the daughter board 236. Additional structure 244 may be provided to support the mother board 220 and daughter board 236, as well as to house the battery power supply 224.

Figure 3A:
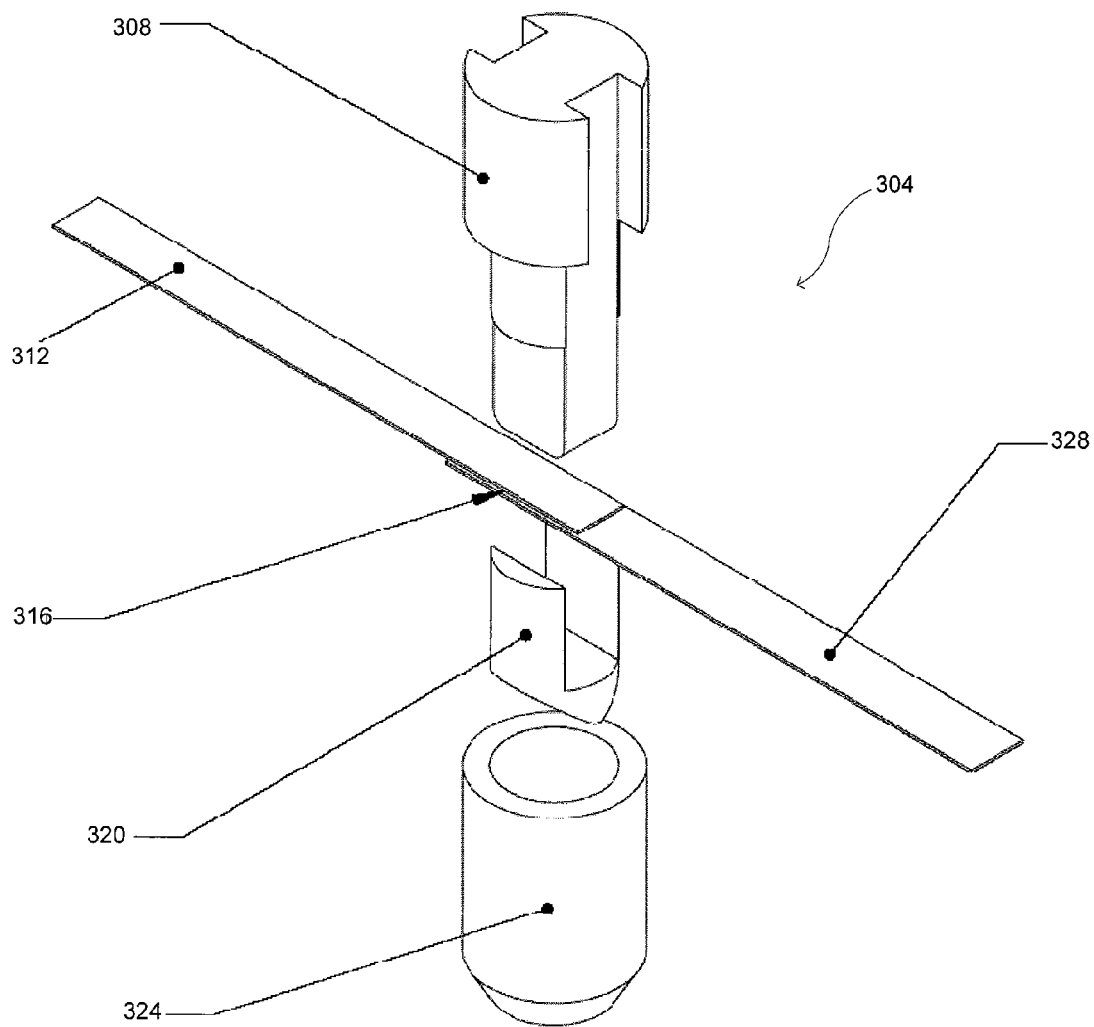
FIGS. 3A and 3B are illustrations of structures for transducer designs that may be used with the devices of FIGS. 1A-2B in different embodiments.
Figure 3B:
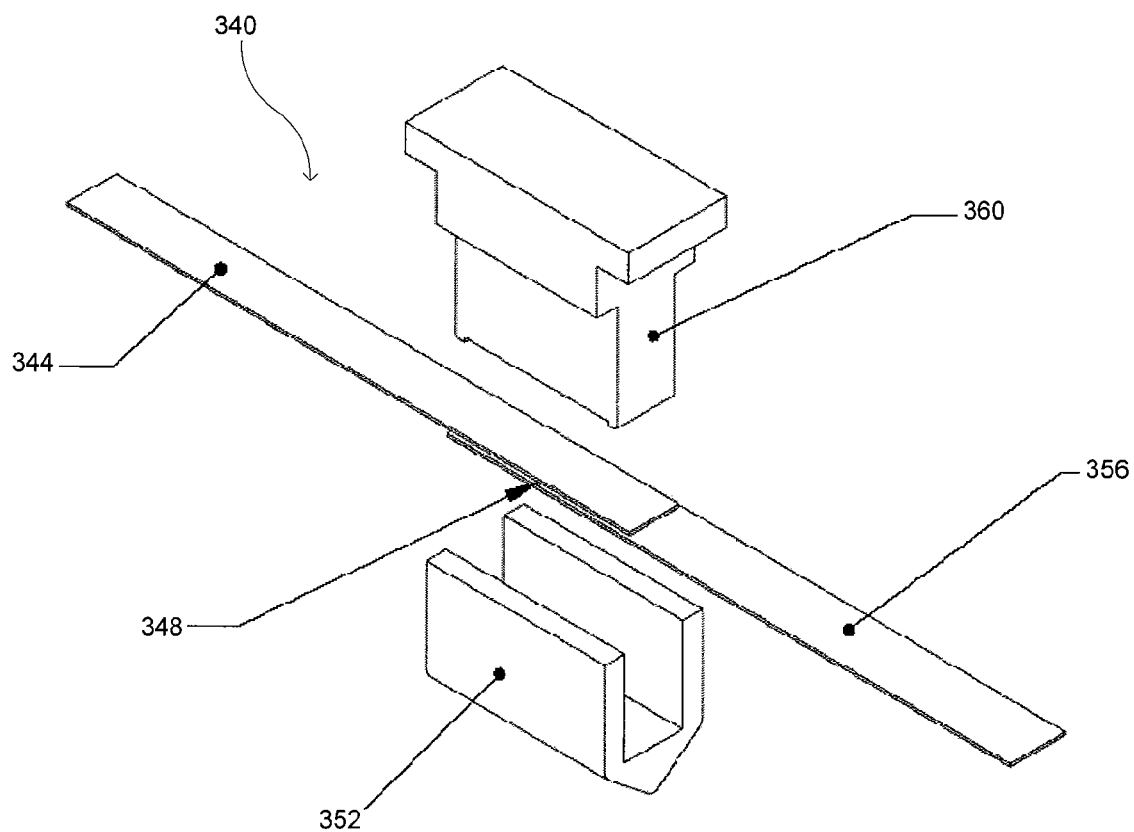

Examples of transducer structures that may be used in embodiments of the invention for the transducer 120 shown in FIG. 1B or for the transducer 212 shown in FIG. 2B are illustrated in greater detail in FIGS. 3A and 3B. While the active part of the transducer may be fabricated from any of a variety of different piezoelectric and other materials, in one embodiment it is fabricated from polyvinylidene fluoride ("PVDF"). This material generally has better acoustic behavior as a receiver than it does as a transmitter, which is acceptable with the types of applications described herein. PVDF is also advantageously broadband. The PVDF portion of the transducer generally has a thickness on the order of tens of μm, with it having a thickness of about 25 μm in one embodiment. One general consideration in the design of the transducer structures is the size of contact between the test-device transducer and the acoustic-device elements. A disadvantage with having too small an area of contact relative to the element size is a reduction in signal level, but too large an area of contact makes it more difficult for the testing device to select out individual elements. The inventors have found that a structure having a generally peaked structure with an elevational contact width less than about 1 cm, and between 0.1 and 0.5 cm in some embodiments, works well for testing most acoustic devices. The generally peaked structure may advantageously include some curvature or flatness to ensure good contact. If the elevational contact width is greater than about 1 cm, echoes may be picked up from neighboring elements, even though the theoretical acoustic-energy coupling might be greater. The elevational size may also accommodate an operator's ability to orient the transducer parallel to the elements of the array being tested. The azimuthal width is generally between 0.1 and 1.0 mm, with an azimuthal width of about 0.2 mm in certain specific embodiments. With these sizes, operation of elements on individual rows of 1.5-dimensional arrays may be readily tested as well.

In the embodiment shown in FIG. 3A, the transducer structure 304 includes a signal lead 312 that comprises the piezoelectric material, such as one-sided poled PVDF, i.e. with conductive plating on one side, and a ground lead 328, which generally comprises an electrical conductor such as copper. The signal lead 312 and ground lead 328 are maintained between two parts of the transducer tip, the upper part 308 being fabricated of molded alumilite in one embodiment and the lower part 320 being fabricated of machined polycarbonate. The signal lead 312 and ground lead 328 are adhered with an adhesive bond 316. The lower part of the transducer tip 320 has a generally peaked shape (with some curvature), and has an elevational width between 0.1 and 0.5 cm when covered with piezoelectric material such as PVDF (not shown). A shield 324, made of copper in one embodiment, may be provided in some embodiments.

The embodiment shown in FIG. 3B provides a similar contact area with the piezoelectric material, but has a generally rectangular cross section that contrasts with the generally circular cross section of the structure 304 shown in FIG. 3A. In this embodiment, the transducer structure 340 again includes a signal lead 344 that comprises the piezoelectric material and a ground lead 356 that comprises an electrical conductor, adhered with an adhesive bond 348 and disposed between upper and lower parts 360 and 352 of the transducer tip. The upper part 360 of the transducer tip may be fabricated of a material like alumilite and the lower part 352 may be fabricated of a material like polycarbonate. The lower part 352 again has a generally peaked shape (with some curvature), and has an elevational width between 0.1 and 0.5 cm when covered with piezoelectric material. In some instances, the piezoelectric material may be provided with an air gap or folded film for better sensitivity.

2. Testing Device Operation

Figure 4A:
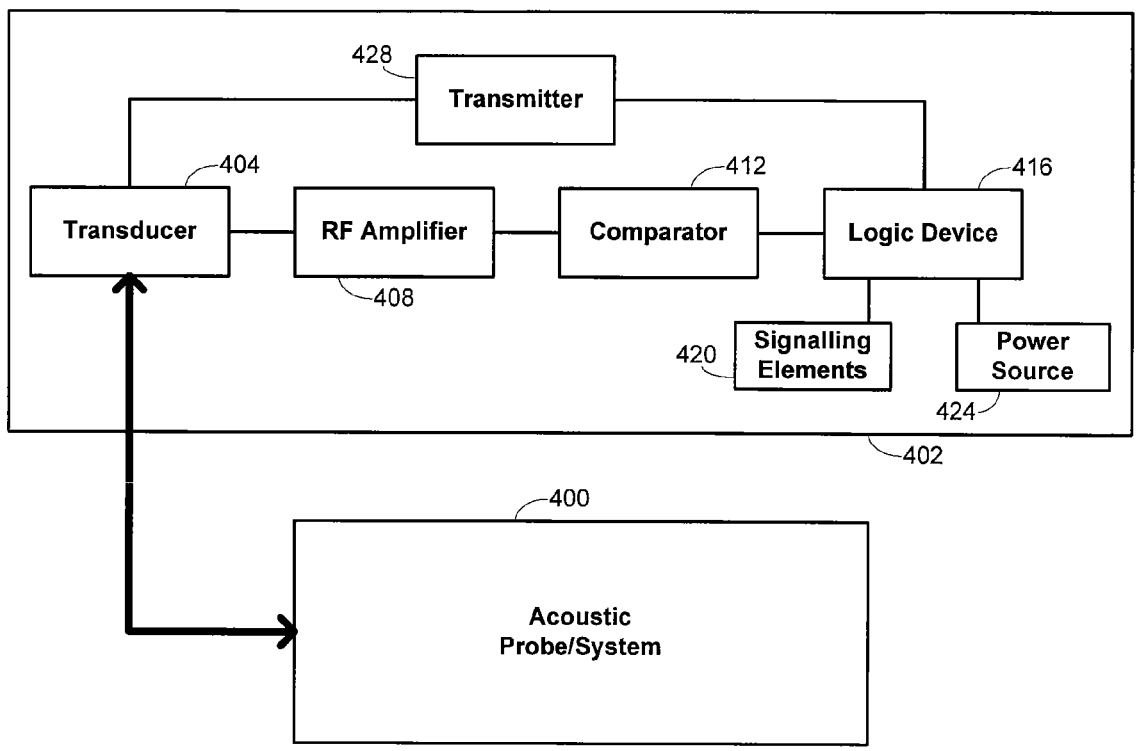
FIGS. 4A-4C are schematic and circuit diagrams illustrating an electrical structure that may be used with the devices of FIGS. 1A-2B in certain embodiments of the invention.

A schematic diagram of a functional structure for the testing device 100 or 200 is provided in FIG. 4A. In this drawing, the testing device is identified generically with reference number 402 and is shown in communication with the acoustic probe or system 400 to be tested, in particular as a result of the operator bringing the transducer 404 into contact with acoustic elements of the probe or system 400 being tested. The functional elements comprised by the testing device 402 may be implemented in a variety of different ways by using suitable electronics and circuitry. The functionality of the testing device 402 is also summarized with the flow diagram of FIG. 5. In describing this functionality, reference is accordingly sometimes made below simultaneously to FIGS. 4A-4C and to FIG. 5.

Figure 5:
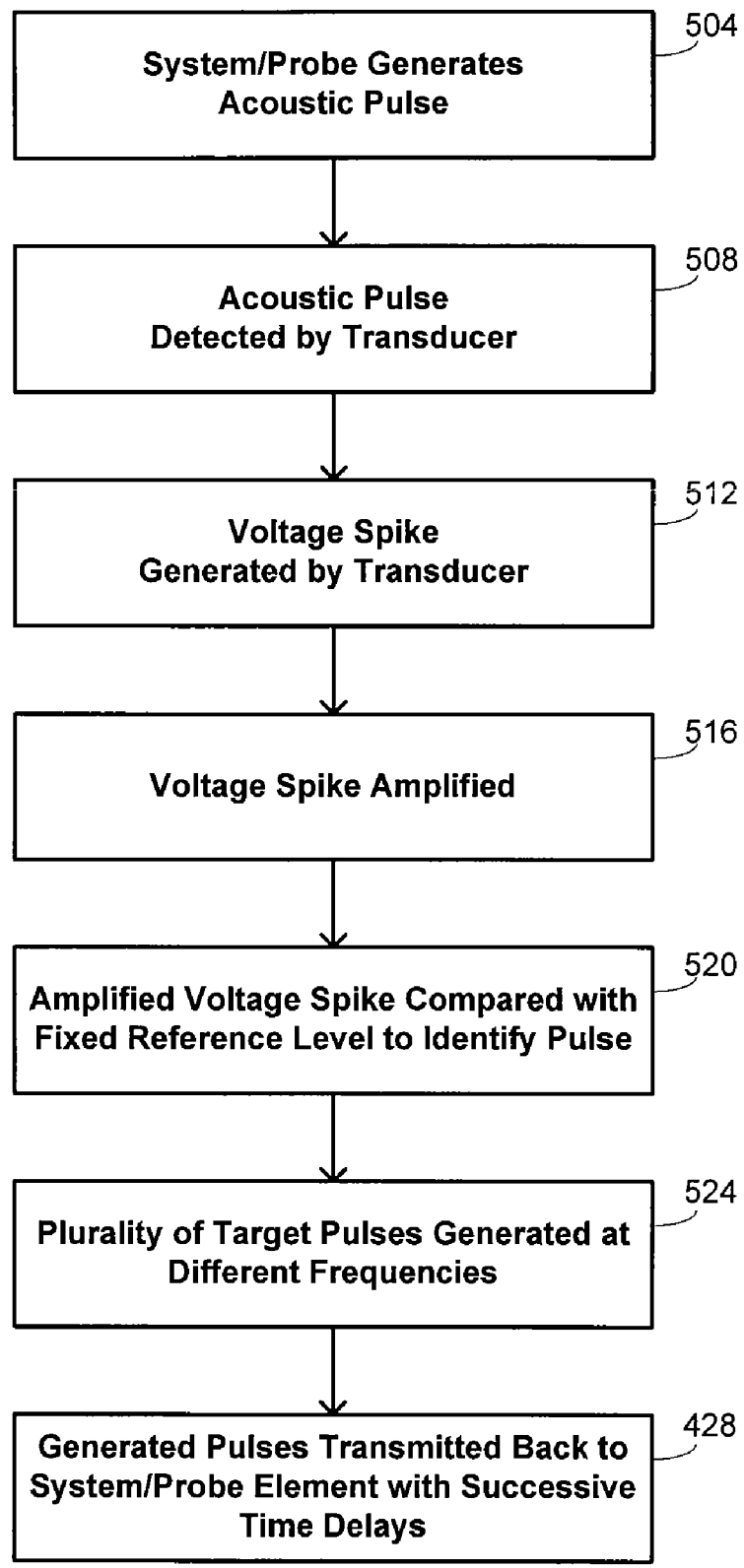
FIG. 5 is a flow diagram summarizing methods of the invention for testing an acoustic probe or system.

With the transducer 404 of the testing device 402 in contact with an acoustic element of the acoustic device 400, the acoustic device 400 generates an acoustic pulse at block 504 of FIG. 5 through the acoustic element. The testing-device transducer 404 detects the acoustic device at block 508 and generates a voltage spike at block 512 as an electrical input to the electrical arrangement comprised by the testing device 402. The voltage spike may advantageously be amplified by an rf amplifier at block 516 and provided to a comparator 412. Merely by way of example, a suitable gain for the amplification may be about 125× in an embodiment, although it will be appreciated by those of skill in the art that other gains, or perhaps even no gain, may be applied depending on the specific electrical characteristics of the testing device 402. The comparator 412 evaluates the strength of the amplified voltage spike relative to a fixed reference level at block 520. Detection of a pulse from the acoustic device 400 being tested is confirmed if the amplified voltage spike has a voltage greater than the fixed reference level.

Decision making is generally coordinated by a logic device 416 provided in communication with other electrical elements of the testing device 402, including a transmitter 428 used to provide a transmit pulse with the transducer 404 back to the acoustic device 400. Signaling elements 420 in the form of color-coded LEDs or other visual or auditory elements are provided, as is a power source 424, which may be in the form or a local battery power source.

Figure 4B:
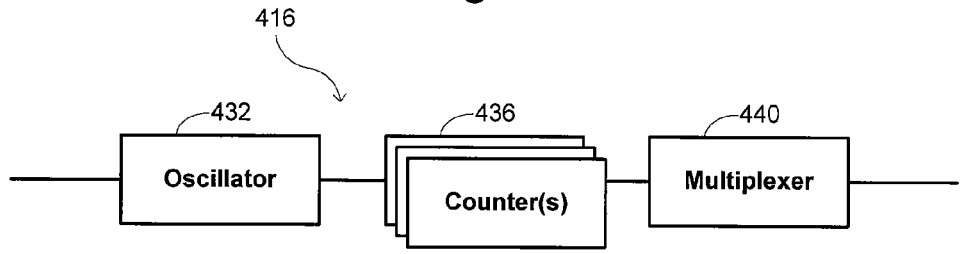

A functional structure for the logic device 416 is illustrated in FIG. 4B and comprises an oscillator 432 used in coordinating generation of a transmit pulse with the transmitter 428 back into the acoustic device 400. The inventors have found that targets that are transmitted back into the acoustic device 400 generally produce trace lines that are more easily identifiable if the target oscillator is started substantially synchronously with the return pulse. The oscillator 432 accordingly drives a counter 436 to generate a return target signal through the transmitter 428. Merely by way of example, a frequency for the oscillator may be about 10 MHz in one embodiment, although other frequencies may be used in alternative embodiments. Also by way of example, the counter 436 may in one embodiment comprise a twelve-bit counter so that the resultant 4096 states correspond to a time interval of 409.6 μs.

In some embodiments, the logic device 416 is configured so that a plurality of target signals are generated with different frequencies, as indicated at block 524 of FIG. 5. Each target signal typically corresponds to a square wave with the same voltage strength and the plurality of signals are multiplexed by multiplexer 404, having been supplied from counters 436 configured to generate respective signals. For instance, each signal may conveniently comprise a ±5V square wave that drives the transducer 404 to transmit respective pulses back into the acoustic device 400. The use of a plurality of pulses at different frequencies advantageously exploits the fact that relevant acoustic devices 400 generally have relatively broadband characteristics. These broadband characteristics mean that elements of the acoustic device 400 will respond to a transmit signal even when the transmit signal is somewhat different from the resonant frequency of the acoustic probe or system. Providing multiple signals at different frequencies thus permits the testing device 402 to be used with a wide range of acoustic devices 400 and their characteristic frequencies. In some embodiments, the electronics comprised by the testing device 402 advantageously separates the plurality of signals in time so that only one pulse of each frequency is transmitted to the acoustic device 300 at any given time in a temporal sequence.

For example, the acoustic devices that an operator may wish to test with the testing device could include a 1.5-MHz ultrasound system and a 15-MHz probe, the two different devices having frequencies separated by an order of magnitude. It will be understood that these numerical values, and those that follow, are provided merely to illustrate the principles involved and are not intended to be limiting; the principles may be applied more generally to acoustic devices having very different frequency characteristics. To accommodate various devices having frequencies between 1.5 MHz and 15 MHz, one embodiment of the invention generates three target signals with frequencies at 10 MHz, 5 MHz, and 2.5 MHz. Such frequencies may be generated with a 10-MHz oscillator 432. An initial delay of 3 cm, corresponding to a typical two-way tissue propagation distance, may be applied to synchronize the target signals to the acoustic device, using 39 µs of the 409.6 µs provided by the counter cycle when the sound speed is 1540 m/s. A first counter 436 may then be used to generate a 10-MHz signal for 1 cm. A second counter 436 may be configured to halve the frequency, generating a subsequent 5-MHz signal for 1 cm. A third counter may be configured to halve the frequency again, generating a subsequent 2.5-MHz signal for 1 cm. A resulting sequence of a 10-MHz, 5-MHz, and 2.5-MHz signal is thus generated by the transmitter 428 for conversion to an acoustic signal by the transducer 404 and transmission back to the acoustic device 400, as indicated at block 528 of FIG. 5. The result is application of pulses to the acoustic device 400 that cover low-frequency, mid-frequency, and high-frequency ranges. In other embodiments, a wider range of frequencies may be covered by generated still a greater number of signals to be transmitted back to the acoustic device 400.

Figure 4C:
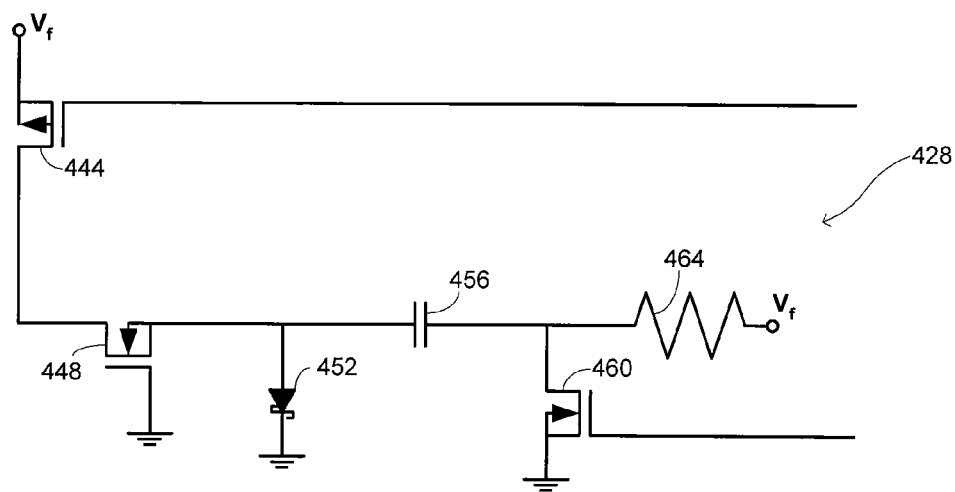

FIG. 4C provides an illustrative structure for the transmitter 428 that may be used in an embodiment that advantageously conserves power while generating return pulses, a feature that may be of particular interest in embodiments that use a local power supply such as a battery. This circuit permits a X volt supply to generate a ±X volt pulse, maintaining a solid clock hold as the battery voltage varies. For example, when using a battery power supply, keeping the supply at 5 V may be a suitable maximum, but to generate enough signal to be recognized 5 V—ground square wave may be somewhat marginal. When the circuit is off, the capacitor 456 is thus charged up to X volts, with current running through the resistor 464 to charge up the left side of the diagram, and flows to ground through the diode 452. When a transmit is started, transistor 460 is used as a switch to short to ground. Because the charge across the capacitor 456 is conserved, the source of transistor 448 substantially immediately drops to −X volts; the fact that the gate of transistor 448 is tied to ground means transistor 448 is on and −X volts is connected right to the transducer. When the square wave shifts to 0 volts, the circuit states go opposite—transistor 460 is turned off, the voltage rapidly jumps to +X volts, causing the output on transistor 444 to driven the output transducer at +X volts.

Figure 6A:
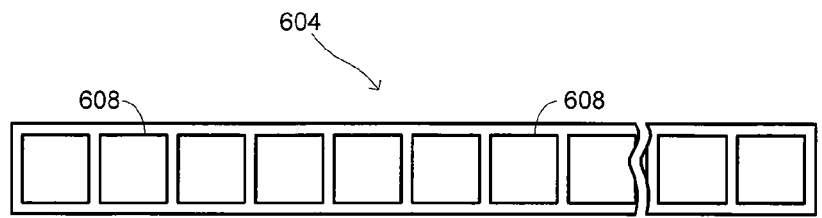
FIGS. 6A-6C are schematic illustrations of different structures for transducer arrays that may be tested using embodiments of the invention.

In addition to being able to accommodate acoustic devices 400 having a variety of different frequency characteristics, embodiments of the invention may accommodate acoustic devices 400 having a variety of different element structures. Examples of such different structures are illustrated schematically in FIGS. 6A-6C. The array 604 shown in FIG. 6A is a conventional one-dimensional array in which individual acoustic elements 608 are distributed along a length to define the array 604. While the length is shown to be linear in the drawing, the length may more generally be curvilinear, with some acoustic devices having curved distributions of acoustic elements 608.

Figure 6B:
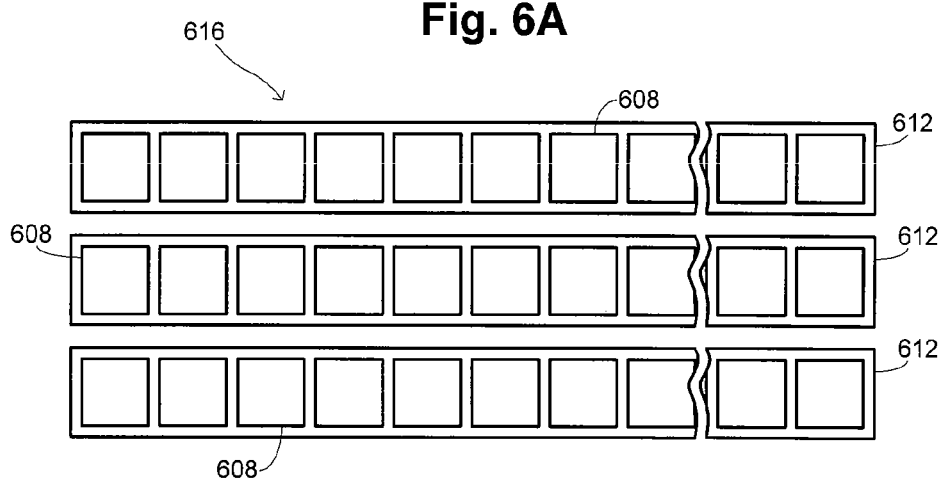

The array 616 shown in FIG. 6B comprises a plurality of one-dimensional arrays 612 spaced along an elevational height. Such an array 616 is sometimes referred to in the art as a "1.5-dimensional array." Acoustic devices having such a 1.5-dimensional array are less successful at near-field imaging, particularly when the elevational height is relatively large, the success of such imaging depending also on the frequency used by the array 616. Accordingly, such arrays 616 sometimes use all of the one-dimensional arrays 612 when imaging the far field, but will use only a smaller subset of the one-dimensional arrays 612, perhaps only a single one-dimensional array 612, when imaging the near field.

Figure 6C:
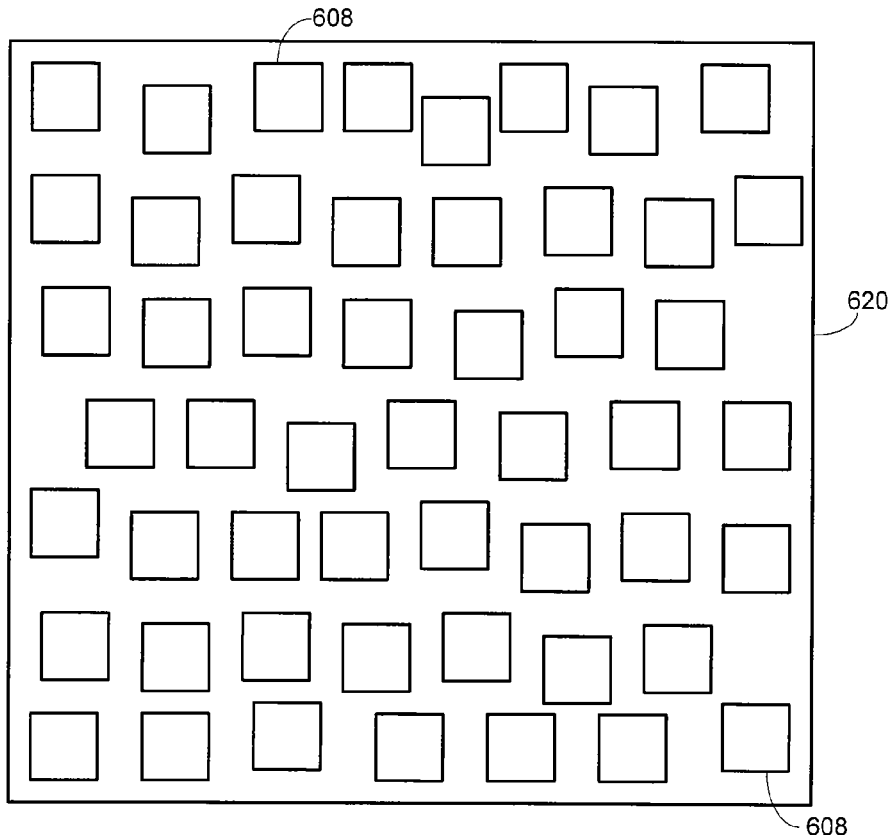

The array 620 shown in FIG. 6C is a two-dimensional array. In this example, the individual acoustic elements 608 are distributed irregularly, with the array 620 being described in the art as a "sparse array." Some two-dimensional arrays may alternatively comprise regularly distributed acoustic elements. While the structures described above for embodiments of the invention may sometimes be more readily used with array structures like those shown in FIGS. 6A and 6B, there is no such general restriction and the invention may be used with array structures like that shown in FIG. 6C, or with still other types of array structures not explicitly illustrated.

3. Exemplary Implementations

Figure 7A:
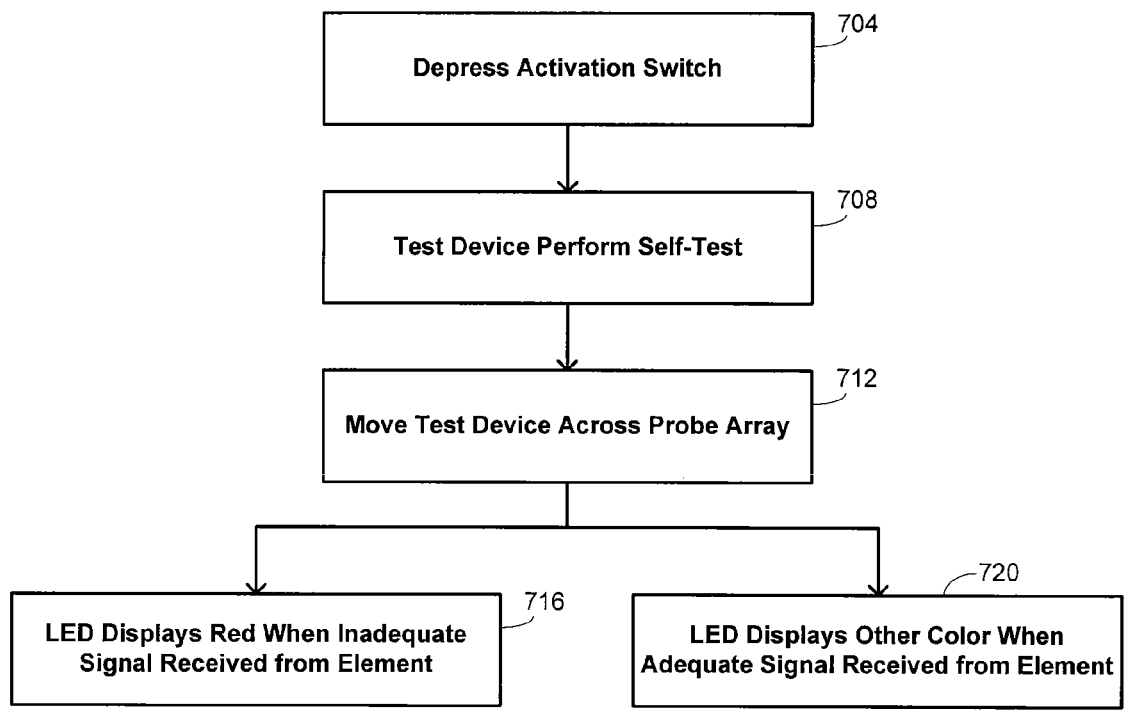
FIG. 7A is a flow diagram summarizing an implementation of methods of the invention in which an acoustic probe is tested.

The testing device described above may be used in a variety of different implementations for testing acoustic probes and/or systems. Some of these implementations are described in detail below. FIG. 7A, for example, is a flow diagram that summarizes methods of using the testing device to evaluate the operation of an acoustic probe. When the activation switch of the testing device is depressed at block 704, a self-test diagnostic may be implemented by the internal electronics at block 708. This may be manifested to a user by initiating a series of changes in the operation of the light-emitting device. For instance, in one implementation, the light-emitting device may quickly turn green and then flash to a steady-state nongreen color such as red. This confirms for the user that at least the green and nongreen modes of operation of the device are functional.

The actual test of the probe is performed by moving the transducer of the testing device across the probe array at block 712. While moving the testing device, the activation switch may be maintained in a depressed state and light pressure applied to ensure good contact between the transducer and the probe being tested. It may be preferable in some embodiments to begin at the middle of the probe array and to move relatively slowly to one side of the array. It is generally preferable for the transducer to be substantially parallel with the probe elements and angled to be in substantially full contact with the face of the array. The effectiveness of the alignment may affect the reliability of the test.

When the probe is being tested, it should be attached to an acoustic system so that the transducer is active. For example, if the acoustic system has a system-freeze configuration, such a configuration should not be activated since no signal is transmitted to the probe when activated. It is also generally preferable for the probe test to be performed when the acoustic system is configured to operate in B mode. Other multiple-mode configurations may be checked as described below. When performing a probe test, it may be sufficient to check probe-element operation by monitoring a status of the light-emitting device on the testing device. In other types of tests described below, monitoring a system display may provide additional information.

As indicated at blocks 716 and 720 of FIG. 7A, the light-emitting device may be configured to display a red color when inadequate signal is being received from the probe element and to display some other color when an adequate signal is received. For instance, in some embodiments, low frame rates cause the light-emitting device to appear to be a pulsating amber or orange color while high frame rates cause it to appear as a steady green color. The blink speed of the light-emitting device may thus be used diagnostically as a qualitative indicator of frame rate and its hue may be used diagnostically as a qualitative indicator of acoustic output power.

Figure 7B:
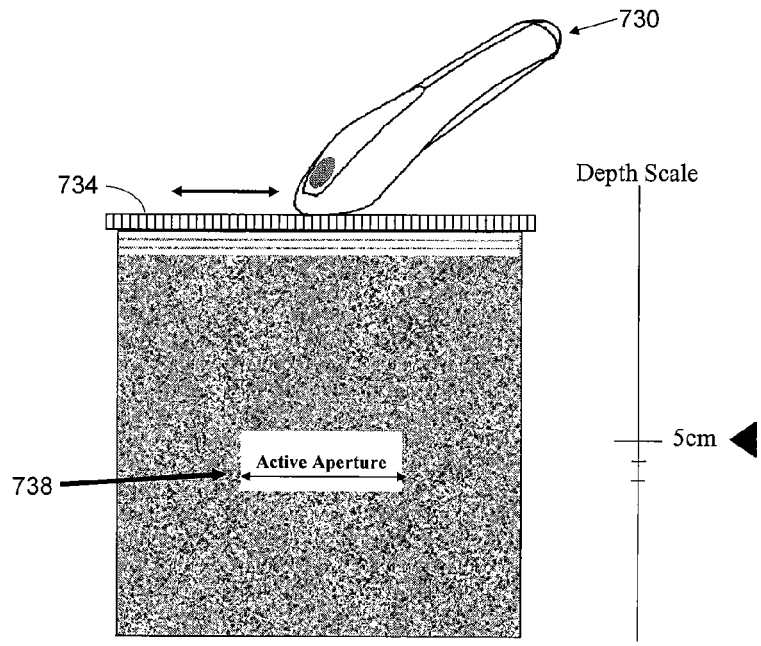
FIG. 7B provides an illustration of testing an acoustic probe with the method of FIG. 7A.

FIG. 7B illustrates the operation of the implementation of FIG. 7A, with a testing device 730 being used to check the operation of a probe array 734. The signal band for the testing device 730 appears as an active aperture 738 that moves with the testing device 730. The system image shown as part of the illustration of FIG. 7B was acquired using an Acuson L5 probe on 128xp10 with NTHI. As evident from the drawing, the B mode depth was set for this test to be 7 cm.

Figure 8A:
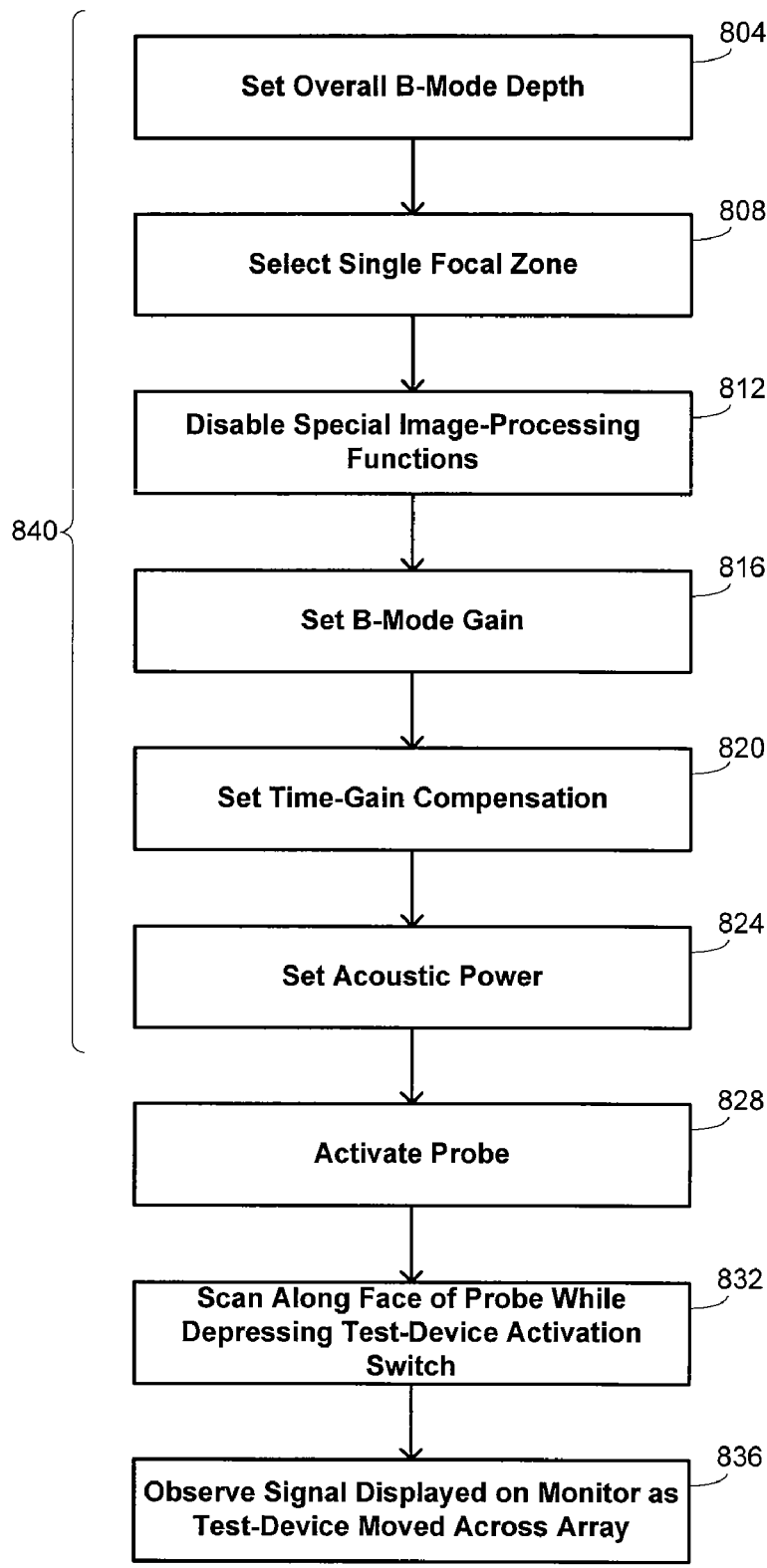
FIG. 8A is a flow diagram summarizing an implementation of methods of the invention in which a B mode of an acoustic system is tested.

FIG. 8A is a flow diagram that summarizes implementations in which the testing device is used to check the B-mode operation of an acoustic system. Blocks 840 of the method correspond to setting specific operational parameters for the acoustic system. The inventors have found greater reliability with certain settings than with other settings. Thus, at block 804, the overall B-mode depth is set. With higher-frequency probes, a B-mode depth of at least 7 cm may be used in some embodiments, and with lower-frequency probes, a B-mode depth of at least 12 cm may be used. A single focal zone may be selected at block 808. This is generally preferable to selecting multiple focal zones, which may introduce electronic switching artifacts in the image. An appropriate focal-zone caret depth in one embodiment is approximately 6 cm. Special image-processing functions are also preferably disabled at block 812 as they may also introduce image artifacts. Examples of such special image-processing functions include second-harmonic imaging and spatial compounding functions, in addition to others. The B-mode gain is set at block 816, an appropriate setting being generally a mid-range setting. The time-gain compensation slide pots are set at block 820, and may be set to maximum. The acoustic power may also be set to maximum at block 824.

Once the operational settings of the system have been established at blocks 840, a probe may be selected and activated from the system at block 828. As in the description of the probe test, any system-freeze functionality should be disabled to ensure that signals are transmitted to the activated probe. The mechanics of performing the B-mode test are similar to the mechanics used in performing the probe test: the testing device is placed in the center of the aperture of the active probe and scanned along the face of the probe at block 832. When evaluating the B-mode operation of the acoustic system, though, the signal displayed on the monitor of the system should be observed at block 836. When the probe has previously been tested using the method of FIG. 7A, image dropout on the system monitor can be a diagnostic indicator of a failure in the front-end (scanner) electronics of the ultrasound system, particularly of receivers.

In some instances, the probe and system tests may be partially combined by rechecking probe operation when an image dropout is observed on the system monitor. By confirming that the light-emitting device of the testing device still shows that the input signal is good—such as by illuminating in a green state—the source of the image dropout may be diagnosed as a likely fault in the front-end electronics and not in the probe.

Figure 8B:
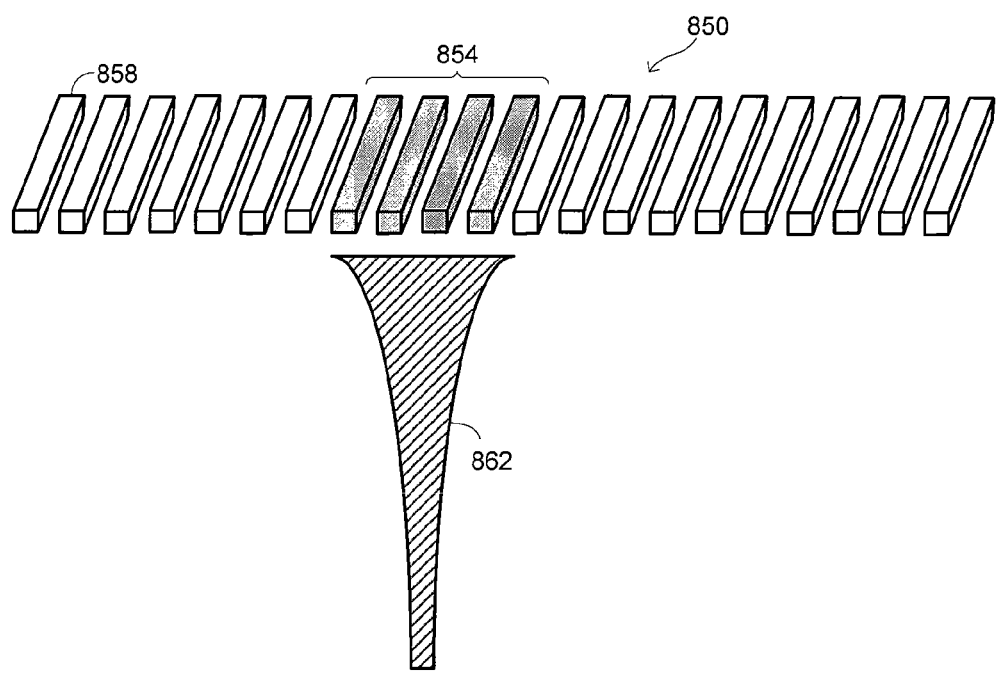
FIG. 8B illustrates the use of a walking aperture to form acoustic lines in system tests.

The form of the display on the system monitor may depend on the type of array comprised by the probe being used. For example, a phased-array probe will display the testing-device signal across most of the sector display because all elements are fired with a phased array. This is generally different from the display that results when a linear or curved array is used since use of those probes will produce a signal from the testing device only within the active aperture. This effect is illustrated schematically in FIG. 8B, where the array of elements 858 is denoted generally by reference number 850. A beam 862 activates an aperture that comprises a subset 854 of the elements 858. Acoustic lines are formed as this aperture is translated across the array 850.

Figure 8C:
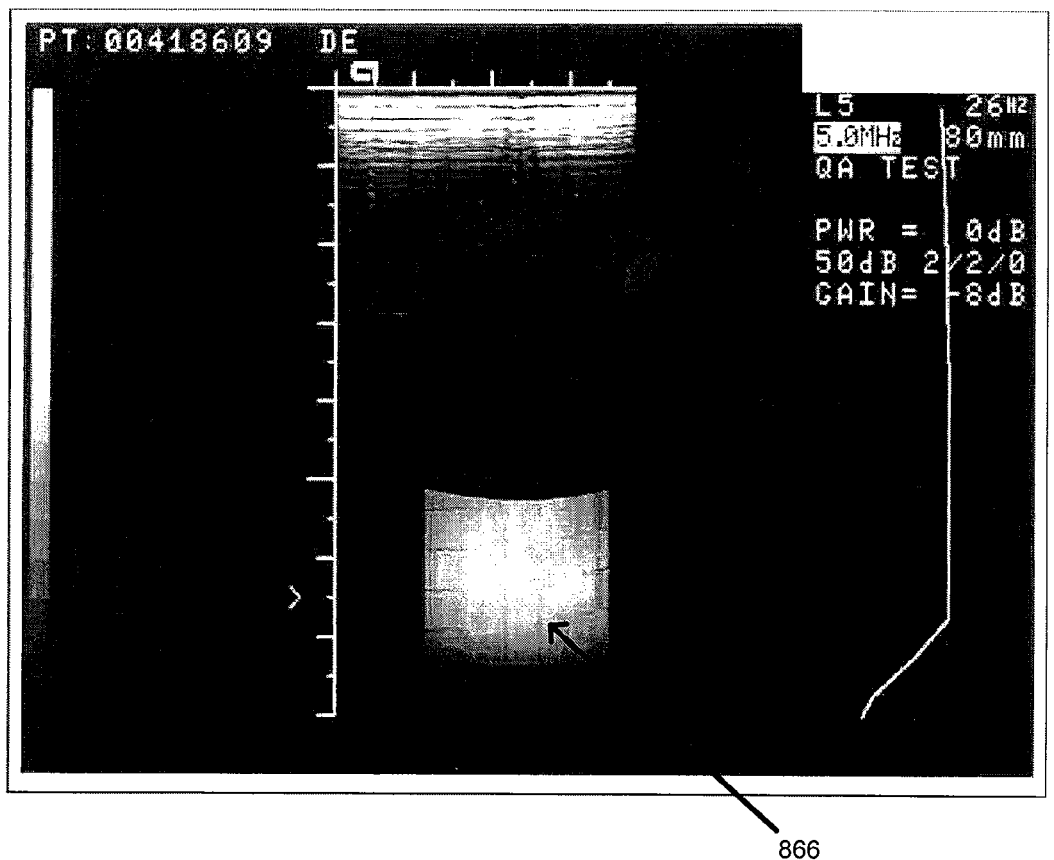
FIGS. 8C and 8D provide examples of screen views on an acoustic system when performing the method of FIG. 8A.
Figure 8D:
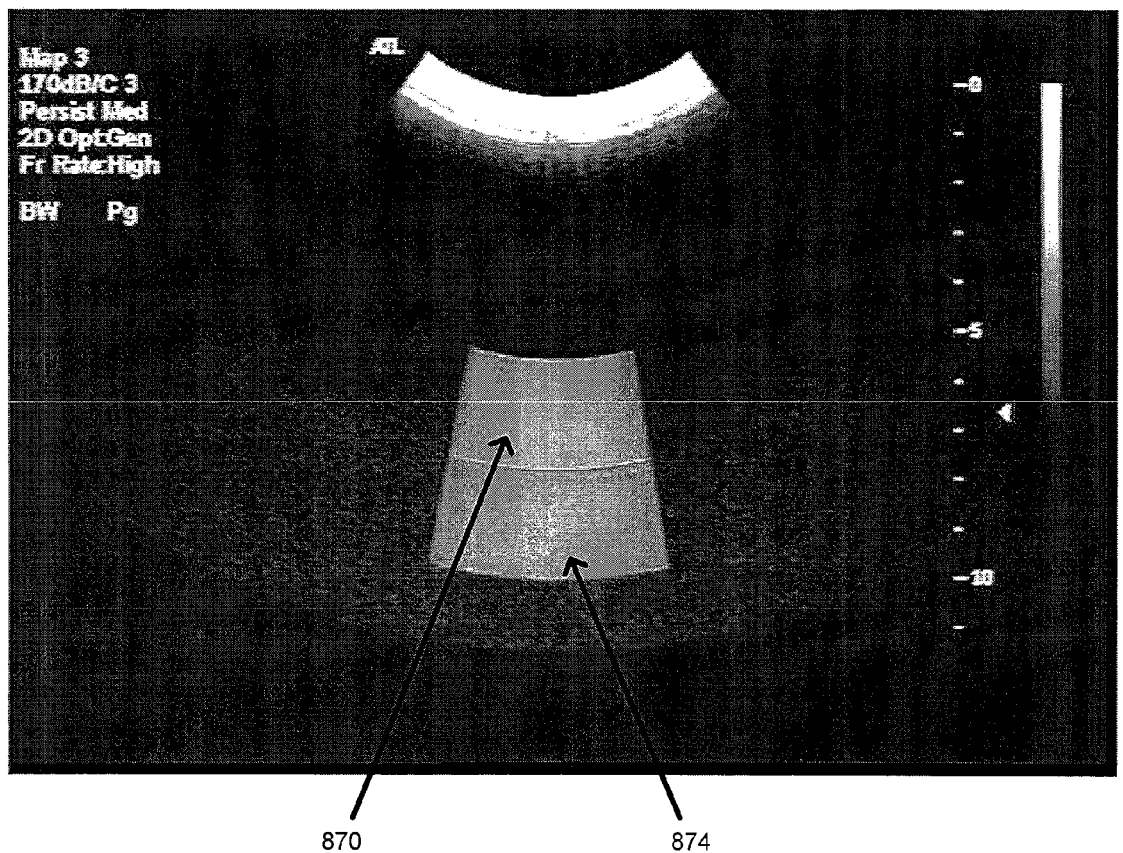

Examples of the displays that may result when a curved or linear array is used are shown with the system screen views of FIGS. 8C and 8D. In FIG. 8C, the acoustic lines are formed as an active aperture 866. This example shows results for a narrowband probe, with only a single 5-MHz signal displayed. In cases where a broadband probe is used, the active aperture seen on the display may comprise a plurality of distinct bands. This is evident, for example, in FIG. 8D, where a 5-MHz band 870 is observed distinctly from a 2.5-MHz band 874.

Figure 9A:
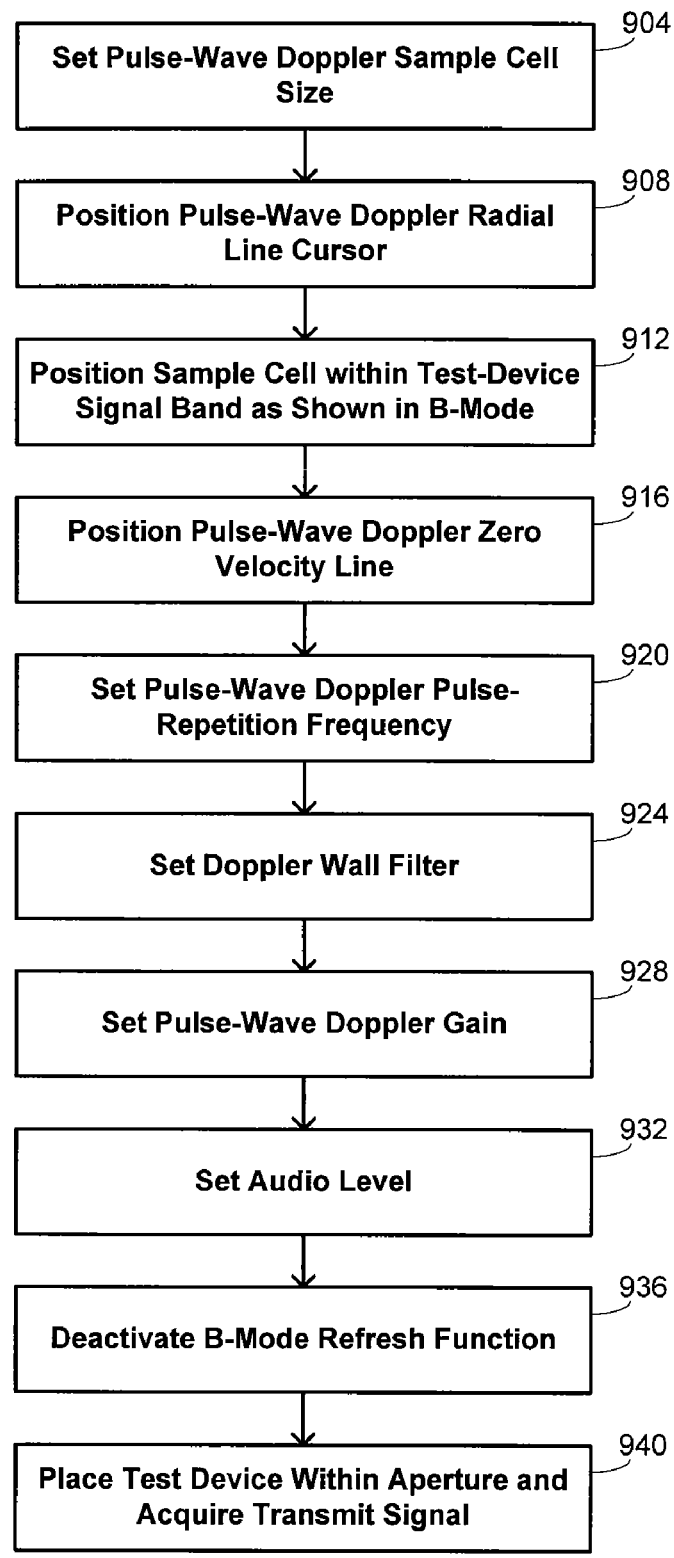
FIG. 9A is a flow diagram summarizing an implementation of methods of the invention in which a Doppler mode of an acoustic system is tested.
Figure 9B:
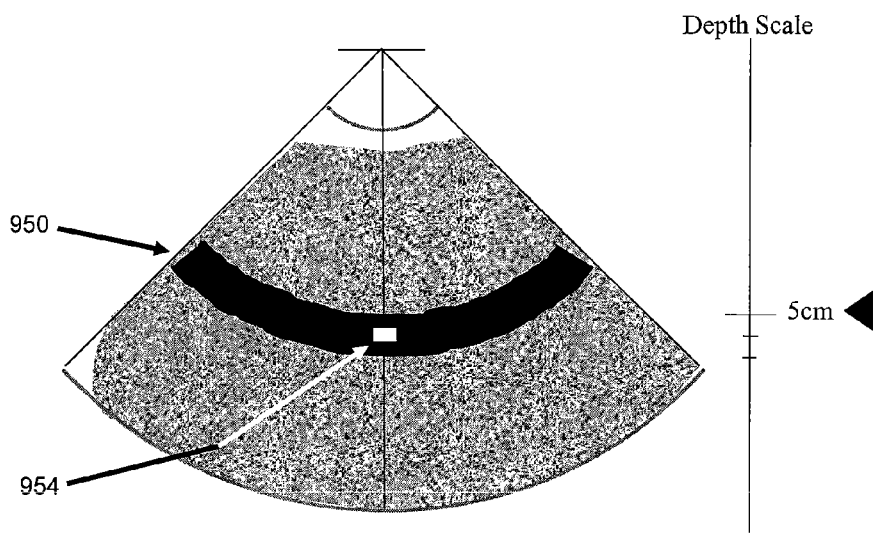
FIG. 9B illustrates an exemplary cell placement for testing a Doppler mode of an acoustic system.

FIG. 9A is a flow diagram that summarizes implementations in which the testing device may be used to evaluate pulsed-wave ("PW") Doppler performance of acoustic systems. Similar to FIG. 8A, several of the blocks in the diagram correspond to putting the acoustic system to be tested into a state appropriate for performing the test. For example, at block 904, the PW Doppler sample cell size is set. Usually, a small sample cell size is preferred and it is appropriate in many embodiments for the sample cell size to be set to its minimum value for the system. On many systems, the minimum sample cell size is 1 mm. At block 908, the PW Doppler radial line cursor is positioned. While there are different positions that can be used in different embodiments, positioning the cursor near the middle of the sector or linear display may generate more reliable test results. As indicated at block 912, the sample cell is positioned within the test-device signal band as shown in the B mode. This sample-cell placement is illustrated in FIG. 9B. The test-device signal band is denoted by reference number 950 and the sample cell 954 is positioned within the band 950. In this illustration, the sample cell 950 has been minimized and positioned in the middle of the signal band 954, providing an effective configuration for generating reliable test results.

Figure 9C:
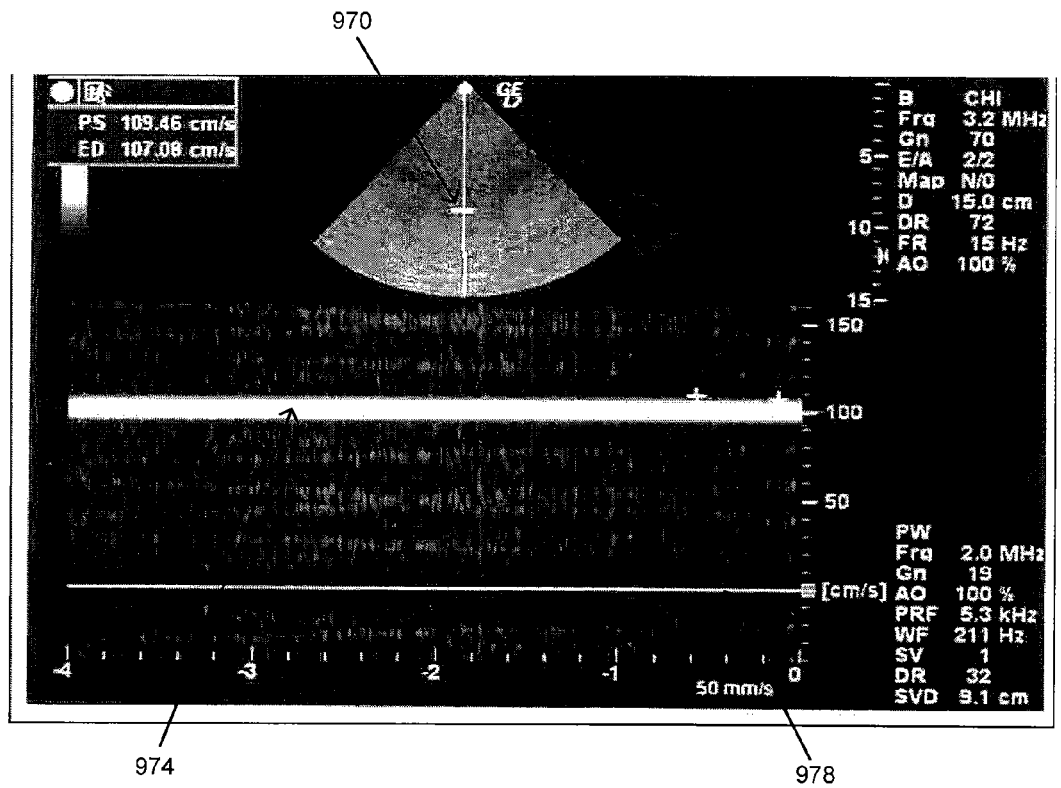
FIG. 9C provides an example of a screen view on an acoustic system when performing the method of FIG. 9A.

The pulse-wave zero-velocity line, which is sometimes alternatively referred to in the art as the "baseline" is set at block 916. It is preferable that the zero-velocity line be set so that a majority of the vertical scale on the display is shown in the positive direction, but showing a major increment of negative scale. A suitable positioning of the zero-velocity line is illustrated in FIG. 9C, which provides an example of a display generated on a system monitor during a test of its Doppler mode. The zero-velocity line is identified with reference number 978 and the image also shows the positioning of the sample cell 970.

At block 920 of FIG. 9A, the PW Doppler pulse repetition frequency is set. The best value for the repetition frequency may depend on specific characteristics of the acoustic system being tested, but suitable values for many systems are within the range of 5.3 kHz to 6.5 kHz. The Doppler wall filter is set at block 924. Again, the best value is dependent on the specific system being tested, but suitable values for the wall filter are about 200 Hz. The PW Doppler gain is set at block 928, preferably just to the point at which speckle noise is observable in the display. This is typically at a mid range of the system capacity. The audio level is set at block 932 and may also be set at about a mid range of the system capacity.

With these settings established, the B-mode refresh mode may be deactivated at block 936, ensuring that the B-mode image is frozen. The test device is then placed within the aperture, preferably near the middle of the aperture, and activated so that a transmit signal is received, as indicated at block 940. When the Doppler mode of the system being tested is operating normally, a corresponding signal appears in the display and is audible. The velocity of the signal depends on the Doppler frequency of the probe, but is typically in the range of 30 cm/s-1.2 m/s. The appearance of the Doppler signal is shown in the exemplary display of FIG. 9C as signal 974.

Figure 10A:
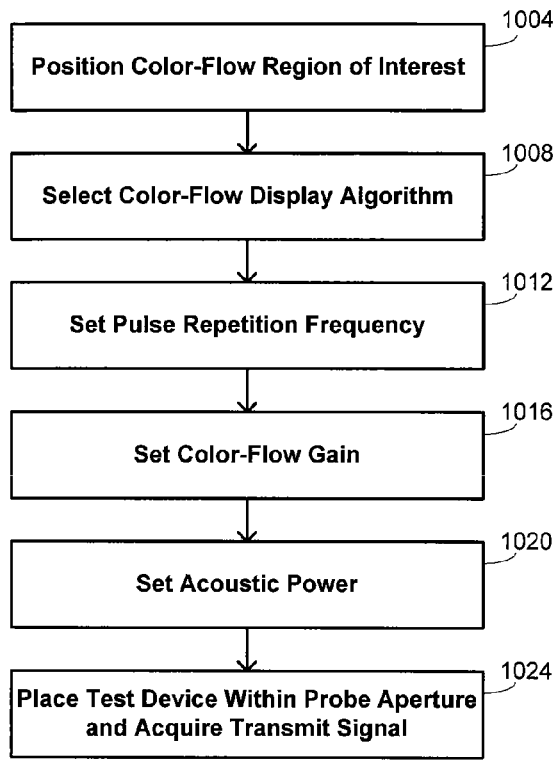
FIG. 10A is a flow diagram summarizing an implementation of methods of the invention in which a color-flow mode of an acoustic system is tested.
Figure 10B:
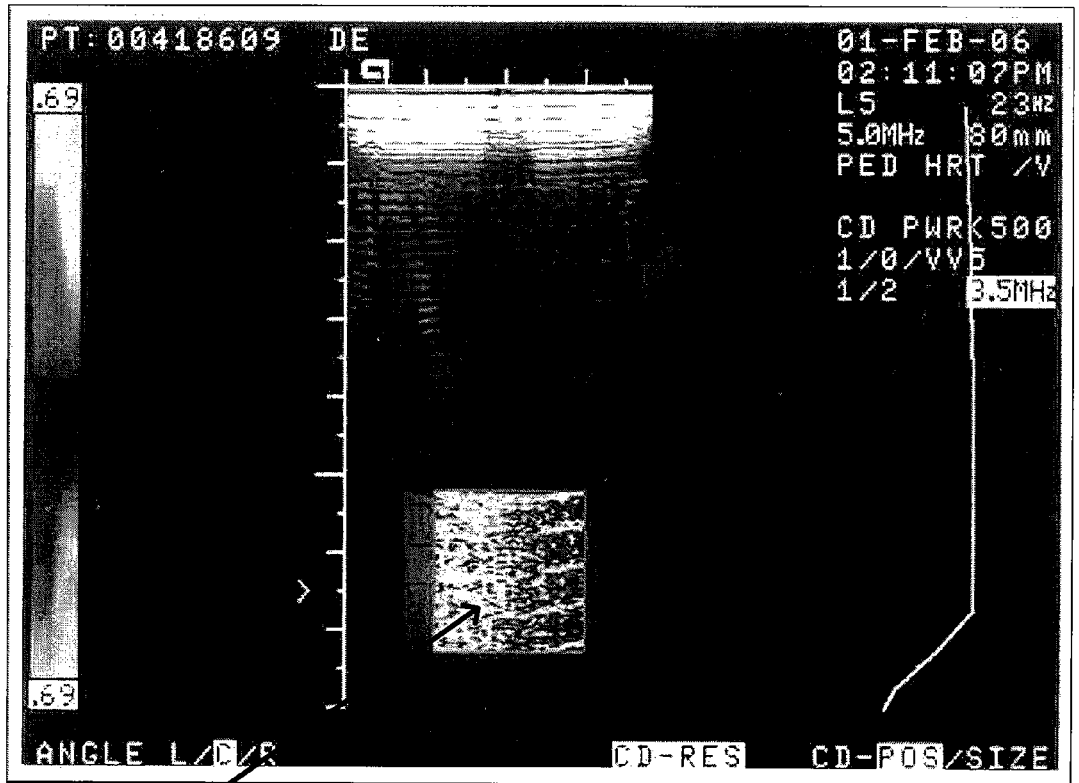
FIG. 10B provides an example of a screen view on an acoustic system when performing the method of FIG. 10A.

The flow diagram of FIG. 10 summarizes implementations in which methods of the invention are used to evaluate the performance of color-flow modes of acoustic systems. The process begins by positioning the color-flow region of interest at block 1004. Similar to the positioning of the sample cell for Doppler testing, the color-flow region of interest is preferably positioned near the middle of the B-mode image band for the testing device. This is illustrated in FIG. 10B, which shows an exemplary screen display of an acoustic system undergoing a color-flow test; the region of interest is denoted by reference number 1030. At block 1008 of FIG. 10B, the color-flow display algorithm is selected. Many acoustic systems have a number of different color-flow display algorithms that may be used. A pulse repetition frequency that is set at block 1012 is preferably relatively high. The color-flow gain is set at block 1016. Again similar to the process used for testing Doppler modes of operation, the color-flow gain is preferable set to the point where color-flow noise speckle is just seen within the region of interest. The acoustic power is set at block 1020 and is preferably maximized.

With the system settings thus configured, the testing device is placed within the probe aperture at block 1024 so that a transmit signal may be acquired. The testing device is preferably positioned near the center of the aperture. The color flow signal may then be observed within the region of interest as seen in FIG. 10B.

Figure 11A:
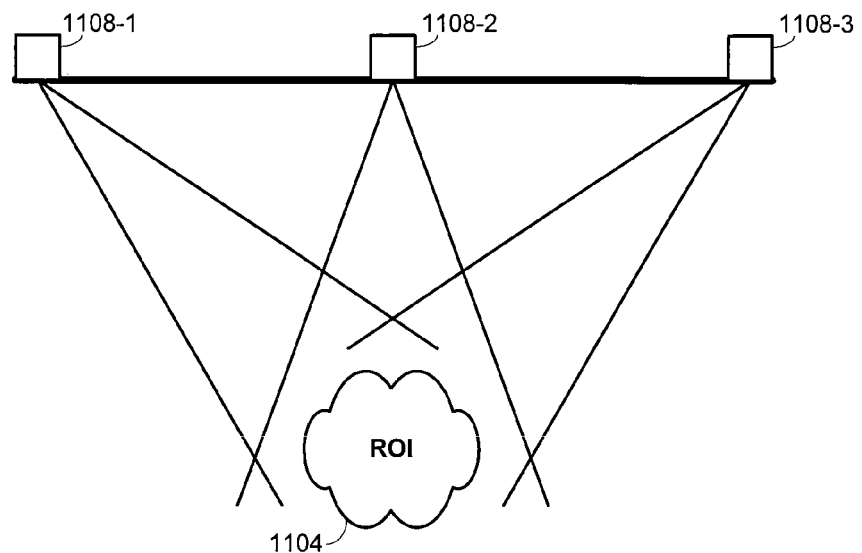
FIG. 11A is a schematic illustration of spatial compounding techniques.

Embodiments of the invention also permit evaluation of spatial-compounding modes. Spatial compounding is a technique that may be used to reduce speckle noise by combining partially correlated or noncorrelated images of the same region of interest produced by transducers with different spatial locations. The technique is illustrated schematically in FIG. 11A, with transducers 1108 being used to image a region of interest 1104 with an acoustic imaging technique. There are a variety of ways in which the different images may be compound. For example, with the images from each transducer denoted as $I_j$, each of the following is a potentially useful compounding technique:

$$\text{Average compounding: } I = \frac{1}{N}\sum_{j=1}^{N} I_j;$$

$$\text{Root-mean-square compounding: } I = \sqrt{\frac{1}{N}\sum_{j=1}^{N} I_j^2};$$

-continued $$\text{Log-compression compounding: } I\left[\prod_{j=1}^{N} I_j\right]^{1/N}.$$

Irrespective of the specific compounding technique that is used, the functionality of a spatial-compounding mode may be checked by using a technique similar to that described in connection with FIGS. 9A and 10A for evaluating Doppler and color-flow modes. In particular, the region of interest is positioned within the B-mode image band, preferably near the middle of the band. After selection of a spatial-compounding mode, the testing device is placed near the center of the probe aperture so that a signal may be acquired.

Figure 11B:
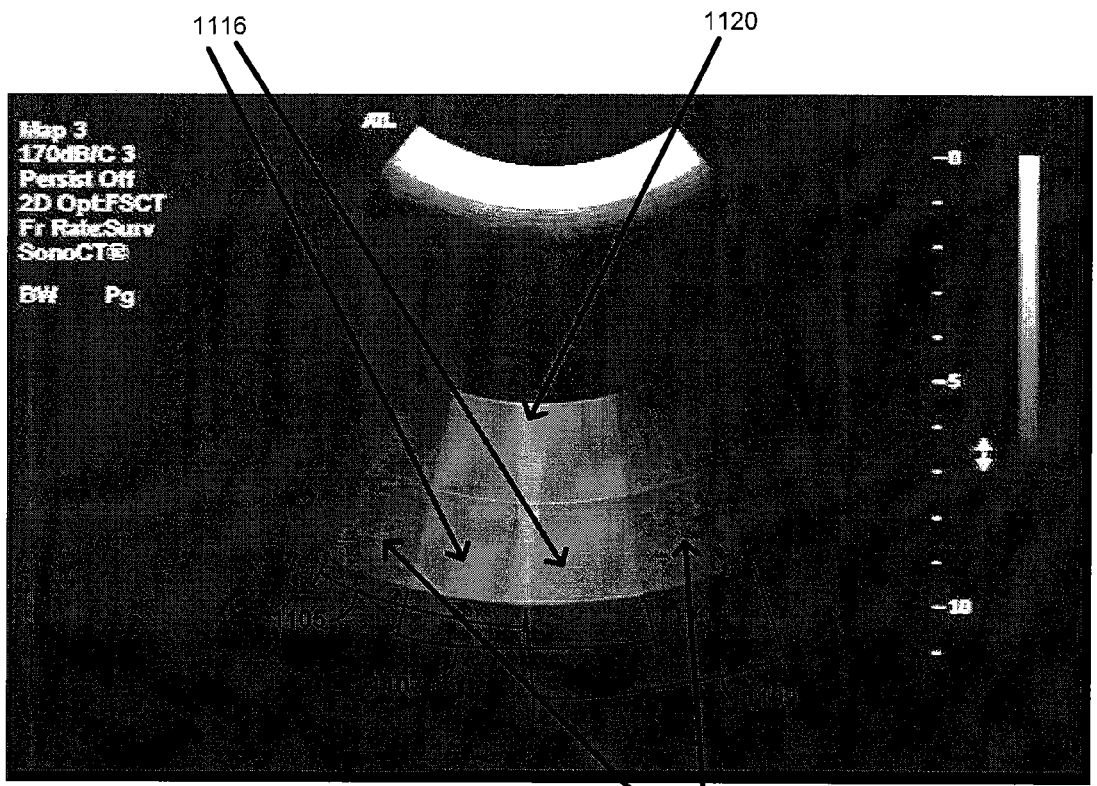
FIG. 11B provides an example of a screen view on an acoustic system in which spatial compounding can be detected.

An example of a screen view produced by such a technique is shown in FIG. 11B. The separate beam structures associated with the spatially distributed transducers is readily detectable because the testing device produces an isolated signal that is not complicated by actual detected image structure. In the illustration of FIG. 11B, for example three separate beams 1105, 1107, and 1109 are evident: two regions 1112 have relatively low intensity because they include contributions from only a single beam (beam 1105 or beam 1109); two regions 1116 have intermediate intensity because they include contributions from two beams (the combination of beams 1105 and 1107 or the combination of beams 1107 and 1109); and one region 1120 has a strong intensity because it includes contributions from all three beams 1105, 1107, and 1109.

Embodiments of the invention thus permit a wide array of different modalities of acoustic systems to be tested with the testing device. Even though these different modalities have very different operational characteristics, the same testing device may be used. Furthermore, the different modalities that have been described are merely exemplary of the kinds of modalities that may be tested using the testing device. Still other types of modalities of acoustic systems that have not been specifically described may also be tested, such as M mode, second-harmonic imaging, temporal compounding, dynamic focusing, and other operational modes. The different modalities may be provided with electronics comprised by the acoustic system but disposed on different boards; the ability to test different modalities thus enables operational faults of the acoustic system to be diagnostically allocated to different boards.

In much of the foregoing description, reference has been made to flow diagrams that summarize certain methods that may be implemented in embodiments of the invention. While such flow diagrams identify specific steps and show an exemplary order in which those steps may be performed, it is noted that neither of these is intended to be limiting. The steps that are shown may be performed in a different order in different embodiments. In addition, some of the steps may be omitted in certain embodiments or additional steps that are not explicitly shown may be added in other embodiments.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A hand-held testing device for testing operation of acoustic elements comprised by an acoustic device, the hand-held testing device comprising:

a housing;

a power supply local to the housing;

an acoustic transducer; and circuitry disposed within the housing and provided in electrical communication with the power supply and with the acoustic transducer, wherein the circuitry is configured to identify production of a voltage pulse by the acoustic transducer in response to receipt of a received acoustic signal by the acoustic transducer from one of the acoustic elements and to operate the transducer to transmit a transmitted acoustic signal to the one of the acoustic elements.

2. The hand-held testing device recited in claim 1 wherein the acoustic transducer consists of a single acoustic transducer.

3. The hand-held testing device recited in claim 1 wherein the transmitted acoustic signal comprises a plurality of transmitted acoustic signals having different frequencies.

4. The hand-held testing device recited in claim 3 wherein the circuitry is further configured to operate the transducer to transmit the plurality of transmitted acoustic signals successively in time.

5. The hand-held testing device recited in claim 1 wherein the circuitry is disposed on a mother board and a daughter board connected with the mother board with a notch assembly.

6. The hand-held testing device recited in claim 1 wherein the acoustic transducer is shaped and sized to contact the acoustic elements individually.

7. The hand-held testing device recited in claim 1 wherein the acoustic transducer has a generally peak-shaped tip for contacting the acoustic elements.

8. A hand-held testing device for testing operation of acoustic elements comprised by an acoustic device, the hand-held testing device comprising:

a housing;

a power supply local to the housing;

an acoustic transducer; and circuitry disposed within the housing and provided in electrical communication with the power supply and with the acoustic transducer, wherein the circuitry is configured to identify production of a voltage pulse by the acoustic transducer in response to receipt of a received acoustic signal by the acoustic transducer from one of the acoustic elements and to operate the transducer to transmit a transmitted acoustic signal to the one of the acoustic elements;

wherein a tip has an elevational length less than about 1 cm.

9. A hand-held testing device for testing operation of acoustic elements comprised by an acoustic device, the hand-held testing device comprising:

a housing;

a power supply local to the housing;

an acoustic transducer; and circuitry disposed within the housing and provided in electrical communication with the power supply and with the acoustic transducer, wherein the circuitry is configured to identify production of a voltage pulse by the acoustic transducer in response to receipt of a received acoustic signal by the acoustic transducer from one of the acoustic elements and to operate the transducer to transmit a transmitted acoustic signal to the one of the acoustic elements;

wherein a tip has an elevational length between 0.1 and 0.5 cm.

10. The hand-held testing device recited in claim 7 wherein the tip comprises polyvinylidene fluoride.

11. A hand-held testing device for testing operation of acoustic elements comprised by an acoustic device, the hand-held testing device comprising:

a housing;

a power supply local to the housing;

an acoustic transducer;

circuitry disposed within the housing and provided in electrical communication with the power supply and with the acoustic transducer, wherein the circuitry is configured to identify production of a voltage pulse by the acoustic transducer in response to receipt of a received acoustic signal by the acoustic transducer from one of the acoustic elements and to operate the transducer to transmit a transmitted acoustic signal to the one of the acoustic elements; and a signaling element provided in electrical communication with the circuitry, wherein the circuitry is further configured to identify production of the voltage pulse by placing the signaling element into a predetermined state.

12. The hand-held testing device recited in claim 11 wherein:

the signaling element comprises a plurality of predetermined states; and the circuitry is further configured to identify a failure to produce the voltage pulse by placing the signaling element into a second of the predetermined states.

13. The hand-held testing device recited in claim 11 wherein the signaling element comprises a light-emitting diode.

14. The hand-held testing device recited in claim 1 wherein the housing is generally cylindrical, having a diameter between about 0.2 cm and 5.0 cm and a length between about 4 cm and 30 cm.

15. The testing device recited in claim 1 wherein the circuitry is configured to operate the transducer to transmit the transmitted acoustic signal to the one of the acoustic elements substantially synchronously with receipt of the received acoustic signal by the acoustic transducer.

* * * * *